(12) United States Patent
Harrington et al.

(10) Patent No.: US 6,323,344 B1
(45) Date of Patent: Nov. 27, 2001

(54) PREPARATION OF KETOROLAC

(75) Inventors: Peter J. Harrington; Hiralal N. Khatri, both of Louisville; George C. Schloemer, Longmont, all of CO (US)

(73) Assignee: Syntex (U.S.A.) Inc., Palo Alto, CA (US)

( * ) Notice: Subject to any disclaimer, the term of this patent is extended or adjusted under 35 U.S.C. 154(b) by 0 days.

(21) Appl. No.: 09/754,529

(22) Filed: Jan. 1, 2001

Related U.S. Application Data

(62) Division of application No. 09/460,526, filed on Dec. 13, 1999, now Pat. No. 6,197,976.
(60) Provisional application No. 60/112,386, filed on Dec. 14, 1998.

(51) Int. Cl.[7] ................................. C07D 209/52
(52) U.S. Cl. ..................... 548/516; 548/531; 548/539
(58) Field of Search .................. 548/516, 531, 548/539

(56) References Cited

U.S. PATENT DOCUMENTS

| | | | |
|---|---|---|---|
| 4,089,969 | 5/1978 | Muchowski et al. | 424/274 |
| 4,347,186 | 8/1982 | Muchowski et al. | 548/516 |
| 4,353,829 | 10/1982 | Thurber et al. | 260/326.25 |
| 4,496,741 | 1/1985 | Doherty | 548/453 |
| 4,874,871 | 10/1989 | Fleming et al. | 548/543 |

*Primary Examiner*—T. A. Solola
(74) *Attorney, Agent, or Firm*—Heller Ehrman White & McAuliffe LLP

(57) ABSTRACT

5-Benzoyl-2,3-dihydro-1H-pyrrolizine-1-carboxamides of the formula

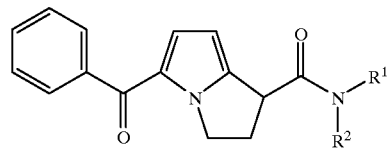

where $R^1$ is alkyl and $R^2$ is optionally substituted phenyl; and the method for their preparation and their conversion to ketorolac and its pharmaceutically acceptable salts.

8 Claims, No Drawings

PREPARATION OF KETOROLAC

CROSS-REFERENCE TO RELATED APPLICATIONS

This application is a divisional of, and claims the benefit under 35 USC 120 and 121 of, U.S. application Ser. No. 09/460,526, filed Dec. 13, 1999, now U.S. Pat. No. 6,197,976. Application Ser. No. 09/460,526 in turn claims the priority under 35 USC 119(e) of Provisional Application No. 60/112,386, filed Dec. 14, 1998. These two applications are incorporated herein by reference.

BACKGROUND OF THE INVENTION

This invention relates to the preparation of ketorolac and its pharmaceutically acceptable salts, especially the trometharnine salt.

U.S. Pat. No. 4,089,969 (to Syntex (U.S.A.) Inc.) discloses various 5-(optionally substituted benzoyl)-2,3-dihydro-1H-pyrrolizine-1-carboxylic acids, including ketorolac, (±)-5-benzoyl-2,3-dihydro-1H-pyrrolizine-1-carboxylic acid, of formula I,

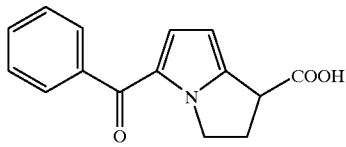

(I)

the tromethamine salt of which is the active ingredient of the anti-inflammatory and analgesic drugs TORADOL® and ACULAR®.

Various methods for the preparation of ketorolac and related pyrrolizine-1-carboxylic acids are exemplified in the patent and chemical literature, and many proceed through a common intermediate, 2,3-dihydro-1H-pyrrolizine-1-carboxylic acid, or its alkyl esters. The alkyl esters may be readily 5-aroylated by methods known to the art, e.g. by Vilsmeier-Haack or Friedel-Crafts aroylations, as described in U.S. Pat. Nos. 4,089,969 and 4,347,186 (also to Syntex (U.S.A.) Inc.), both using dialkylamides; U.S. Pat. No. 4,353,829 (also to Syntex (U.S.A.) Inc.), using morpholides; and in U.S. Pat. No. 4,496,741 (to Merck); and the resulting ester saponified by conventional methods to yield a 5-aroyl-2,3-dihydro-1H-pyrrolizine-1-carboxylic acid.

U.S. Pat. No. 4,874,871 (also to Syntex (U.S.A.) Inc.) discloses a method of preparing 2,3-dihydro-1H-pyrrolizine-1-carboxylic acid and related compounds from pyrrole in the following manner:

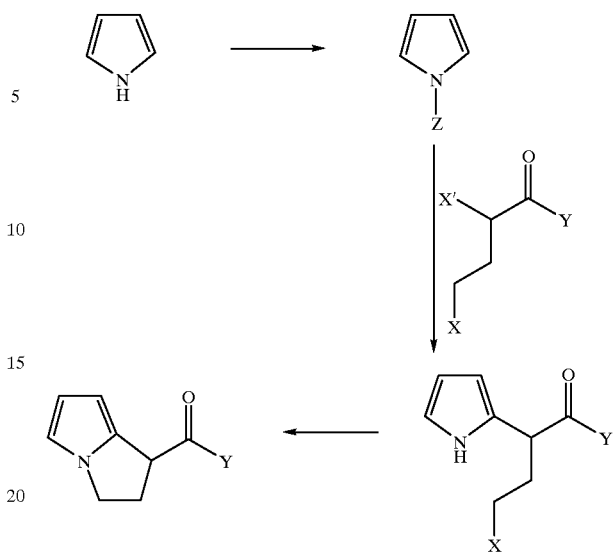

where X and X' are independently halogen;

Y is —OH; —OM⁻M⁺, wherein M is an alkali metal; or —NRR' (where R is lower alkyl and R' is lower alkyl or aryl, or —NRR' is the residue of a saturated cyclic amine); and Z is Li, MgCl, or MgBr.

According to U.S. Pat. No. 4,874,871, the (±)-2,3-dihydro-1H-pyrrolizine-1-carboxamides or salts may be hydrolyzed to the corresponding acid and then converted to the corresponding esters by conventional means; and the esters 5-aroylated and hydrolyzed to afford 5-aroyl-2,3-dihydro-1H-pyrrolizine-1-carboxylic acids by the methods described in U.S. Pat. Nos. 4,089,969; 4,347,186; and 4,353,829.

The disclosures of these patents, and other patents and articles referred to throughout this specification, are incorporated herein by reference.

SUMMARY OF THE INVENTION

In a first aspect, this invention includes 5-benzoyl-2,3-dihydro-1H-pyrrolizine-1-carboxamides of Formula 6,

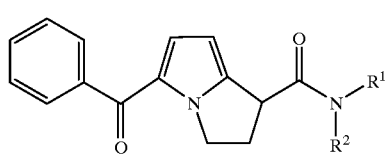

(6)

where $R^1$ is alkyl; and $R^2$ is optionally substituted phenyl.

In a second aspect, this invention includes a method of preparing the 5-benzoyl-2,3-dihydro-1H-pyrrolizine-1-carboxamides of Formula 6.

In a third aspect, this invention includes a method of preparing ketorolac and its pharmaceutically acceptable salts, comprising preparing 5-benzoyl-2,3-dihydro-1H-pyrrolizine-1-carboxamides of Formula 6, followed by hydrolysis, optionally followed by formation of a pharmaceutically acceptable salt.

In a fourth aspect, this invention includes a method of preparing the pyrrolylbutanamides of Formula 3.

In a fifth aspect, this invention includes an improved method of preparing the 2,3-dihydro-1H-pyrrolizine-1-carboxamides of Formula 4.

The preparation may be represented schematically:

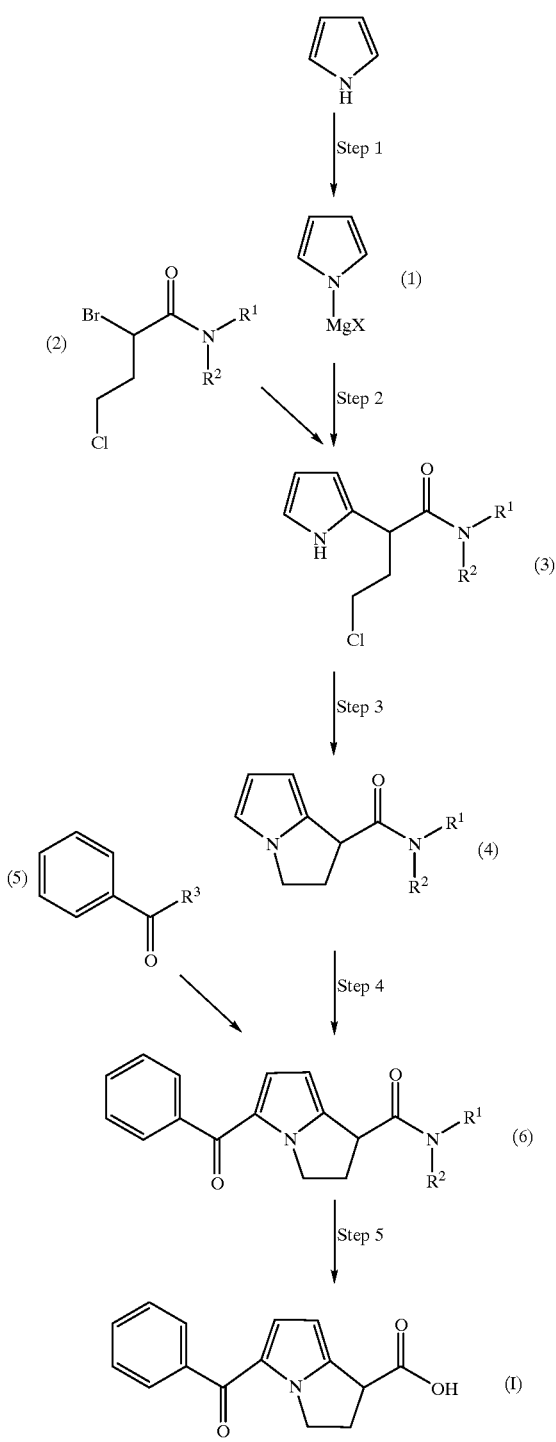

where $R^1$ is alkyl;

$R^2$ is optionally substituted phenyl;

$R^3$ is Cl or —$NR^4R^5$ (where $R^4$ and $R^5$ are independently $C_{3-8}$ alkyl, or —$NR^4R^5$ is morpholino, piperidino, or pyrrolidino); and X is Cl or Br.

DETAILED DESCRIPTION OF THE INVENTION

Definitions

Unless otherwise stated, the following terms used in the specification and claims have the meanings given below:

"Alkanol" means $C_{1-4}$ alcohols such as methanol, ethanol, propanol, isopropanol or butanol. A preferred alkanol is methanol.

"Alkyl" means a straight, branched, or cyclic saturated monovalent hydrocarbon radical having from one to eight carbon atoms, e.g. methyl, ethyl, isopropyl, cyclopropyl, cyclopropylmethyl, and the like. "Lower alkyl" means $C_{1-4}$ alkyl. "Lower alkoxy" means —OR where R is lower alkyl.

"Grignard solvent" means a solvent suitable for the formation of Grignard reagents or their reaction with other reagents. "Grignard solvent" includes ethers such as tetrahydrofuran and diethylene glycol dibutyl ether (butyl diglyme), which may be used as sole solvents, especially in the formation of the pyrrole Grignard reagent of formula 1, and mixtures of such suitable sole solvents, especially tetrahydrofuran, with aprotic cosolvents such as hydrocarbon solvents, e.g. toluene, or polar aprotic solvents such as acetonitrile, N,N-dimethylformamide, N-methyl-2-pyrrolidinone (NMP), tetramethylethylenediamine, 1,3-dimethyl-3,4,5,6-tetrahydro-2(1H)-pyrimidinone (DMPU), 1,3-dimethyl-2-imidazolidinone (DMEU), or ethylene glycol diethers, e.g. 1,2-dimethoxyethane (glyme), diethylene glycol dimethyl ether (diglyme), diethylene glycol diethyl ether, triethylene glycol dimethyl ether (triglyme), tetraethylene glycol dimethyl ether (tetraglyme), which may be used either in the formation of the pyrrole Grignard reagent of formula 1 or, especially, in the formation of the pyrrolylbutanamide of formula 2. Butyl diglyme may be used as a sole solvent in the formation of the pyrrole Grignard reagent and used without addition of aprotic polar cosolvents in the formation of the pyrrolylbutanamide. A preferred cosolvent for tetrahydrofuran is diglyme.

"Hydrocarbon solvent" means aliphatic or aromatic hydrocarbon solvents such as hexane, cyclohexane, toluene, and the like.

"Optionally substituted phenyl" means phenyl optionally substituted with one to three lower alkyl, lower alkoxy, nitro, fluoro, chloro, bromo, or trifluoromethyl substituents.

"Organic solvent" includes the hydrocarbon solvents mentioned above and also includes esters such as ethyl acetate and the like, chlorinated hydrocarbons such as dichloromethane and the like, and the polar aprotic solvents mentioned above.

"Strong base" refers to bases such as alkali metal hydroxides, lower alkoxides, and the like, especially the alkali metal hydroxides.

When a solvent is described as being of a particular type, such as a "Grignard solvent", the term includes not only a "Grignard solvent" as defined, but in addition solvent mixtures containing a Grignard solvent and minor proportions of other solvents (e.g. hydrocarbon solvents), provided that the solvent properties are primarily determined by the type of solvent named.

Starting Materials and Purification

The starting pyrrole and the compounds of formula 2, 3, 4, and 6 may be isolated and purified, if desired, or may be carried into the next reaction step by removing the solvent, using conventional techniques including but not limited to filtration, distillation, crystallization, chromatography, and the like. The compounds may be characterized using conventional means, including physical constants and spectral characteristics. The product ketorolac and its pharmaceutically acceptable salts may be isolated, purified, and characterized similarly.

Compounds 2. The N-alkyl-N-aryl-2-bromo-4-chlorobutanamides of formula 2 may be prepared by methods known to the art. See, for example, West German Patent No. 804 567 (BASF), for the preparation of 2-bromo-4-chlorobutanoyl chloride from α-bromo-γ-butyrolactone. 2-Bromo-4-chlorobutanoyl bromide may be prepared by the bromination of 4-chlorobutanoyl chloride with bromine, as shown in the Example. See also U.S. Pat. No. 4,874,871, referred to previously, for the preparation of the butanamides from the butanoyl halides.

An N-alkyl-arylamine is treated with a 2-bromo-4-chlorobutanoyl halide in the presence of a tertiary amine base such as a trialkylamine and an organic solvent such as toluene. The reaction temperature is maintained at about 10° C. to 80° C. while the addition is allowed to proceed to completion in about 10 minutes to 10 hours. The resulting dihalobutanamide (2) may be isolated by conventional techniques, such as addition of water and acidification of the solution with mineral acid, e.g. hydrochloric acid, separation of the organic and aqueous layers, and evaporation of the solvent; and is used either with or without further purification in Step 2.

The Process

In Step 1, pyrrole is converted to a pyrrole Grignard reagent of formula 1 by methods well known to the art, such as by the reaction of pyrrole with an alkylmagnesium halide such as methylmagnesium chloride, in solution in a Grignard solvent, e.g. tetrahydrofuran or diethylene glycol dibutyl ether. Each of these reagents, for example, is commercially available from suppliers such as Aldrich or Ferro. The reaction is generally performed at reduced temperatures and under an inert atmosphere, e.g. nitrogen, and occurs rapidly, typically within 10 minutes. The resulting pyrrole Grignard reagent (1) is generally used immediately in Step 2.

In Step 2, the dihalobutanamide (2) is contacted with the pyrrole Grignard reagent (1) from Step 1 until the reaction to the N-alkyl-N-aryl-4-chloro-2-(2-pyrrolyl)butanamide of formula 3 is complete. The pyrrole Grignard reagent (1) is preferably present in excess, for example between 1.2-fold and 3-fold excess, typically about a 2-fold excess, over the dihalobutanamide (2) to minimize the formation of 2,5-disubstituted pyrrole products. The reaction is generally performed under an inert atmosphere by the addition of a solution of the dihalobutanamide (2) to a stirred solution of the pyrrole Grignard reagent (1) in a suitable solvent, typically the solvent in which it was formed: however, if the pyrrole Grignard reagent (1) was formed in tetrahydrofuran, desirably a cosolvent is added. The dihalobutanamide (2) may be added to the pyrrole Grignard reagent (1) as a neat material, or as a solution in an organic solvent such as toluene. Preferably, the preparation of the pyrrole Grignard reagent (1) and the alkylation reaction of Step 2 both take place in butyl diglyme, where the alkylation reaction may be accomplished at higher concentrations and solvent recycle is simplified to a single solvent. The reaction temperature may be from about 0° C. to 60° C., but the reaction is slowed by cooling, and addition typically takes place near room temperature, e.g. between about 25° C. and 30° C., in one or more portions, after which the reaction is allowed to proceed to completion. The reaction time may range from 30 minutes to 48 hours, but is ordinarily 2 hours to 10 hours. Following completion of the reaction, the resulting pyrrolylbutanamide (3) may be isolated by conventional techniques, such as addition of water and acidification of the solution with mineral acid, e.g. by addition of concentrated hydrochloric acid to pH 1, followed by separation of the organic and aqueous layers. The organic layer is treated with base, concentrated under reduced pressure, and filtered; and may be used directly in Step 3.

In Step 3, the pyrrolylbutanamide (3) is cyclized to the corresponding N-alkyl-N-aryl-2,3-dihydro-1H-pyrrolizine-1-carboxamide of formula 4. The treated organic layer from Step 2 is added to a stirred suspension of a strong base such as an alkali metal hydroxide, in the presence of a phase transfer catalyst such as ALIQUAT® 336 (tricaprylylmethylammonium chloride) or other quaternary ammonium salt, and a hydrocarbon solvent such as toluene. The reaction temperature is maintained at about 10° C. to 100° C., typically under an inert atmosphere, while the cyclization is allowed to proceed to completion in about 10 minutes to 48 hours. The pyrrolizinecarboxamide (4) may then be recovered by addition of water, separation of the layers and subsequent crystallization from the organic layer.

In Step 4, the N-alkyl-N-aryl-5-benzoyl-2,3-dihydro-1H-pyrrolizine-1-carboxamides of formula 6 are prepared by 5-aroylation methods known to the art, e.g. by the modified Vilsmeier-Haack aroylations described in U.S. Pat. Nos. 4,089,969 and 4,347,186 (using dialkylamides) and U.S. Pat. No. 4,353,829 (using morpholides) for pyrrolizinecarboxylic acid esters, or by Friedel-Crafts aroylation.

In the modified Vilsmeier-Haack aroylation, the pyrrolizinecarboxamide (4) is treated with a mixture of a N,N-disubstituted benzamide such as N,N-dibutylbenzamide, benzmorpholide, or benzoylpiperidine, and an acid chloride, such as oxalyl chloride or phosphorus oxychloride, in an organic solvent, typically a hydrocarbon solvent such as toluene, and the solution is stirred for several hours at elevated temperatures, preferably about 35° C. to 65° C., more preferably about 40° C. to 60° C., especially about 40° C. The solution is stirred for several hours at room temperature and an aqueous alkali metal hydroxide solution is added. Suitable alkali metal hydroxides include lithium hydroxide, sodium hydroxide, and potassium hydroxide. The two-phase mixture is stirred, heated to about 55° C. to 85° C., preferably about 70° C. to 75° C., and the layers separated. The resultant ketorolac-amide (6) may be recovered from the organic layer by acidification with a mineral acid, filtered, and concentrated under vacuum.

In a Friedel-Crafts aroylation, the pyrrolizinecarboxamide (4) is heated to elevated temperature, e.g. reflux temperature, in the presence of an alkali metal carbonate or bicarbonate such as lithium carbonate or lithium bicarbonate, and an organic solvent such as toluene. Benzoyl chloride is added and the mixture is heated for 6 hours to 8 hours. Once the reaction is complete, the reaction mixture is cooled to 70° C. to 80° C., and crystallization of the resulting ketorolac-amide (6) may be effected by addition of hexane; or the resulting ketorolac-amide (6) may be isolated from the reaction mixture in a similar manner to that described above.

The ketorolac-amides (6) are novel, and are useful as intermediates in preparing ketorolac and its pharmaceutically acceptable salts, which are therapeutically useful as discussed above.

In step 5, the ketorolac-amide (6) is hydrolyzed to ketorolac (I); preferably by alkaline hydrolysis using an strong base in an alkanol. The reaction mixture is kept at elevated temperatures, such as at the reflux temperature of the alkanol, e.g. 65° C. for the preferred methanol, for several hours, and then cooled. The ketorolac of formula I may then be isolated by conventional techniques, such as addition of water, extraction with an organic solvent, separation of layers and acidification with a mineral acid, filtered and purified.

Ketorolac (I) may be isolated as the acid, if desired, but will preferably be isolated as a pharmaceutically acceptable salt, especially as the tromethamine salt. The preparation and isolation of ketorolac salts may be performed by conventional methods, such as by treating the ketorolac (acid) with the appropriate base, preferably tromethamine, in an alkanol. The solution is concentrated by partial removal of the alkanol and the product crystallized by the addition of an organic solvent such as ethyl acetate, cooled, filtered, and dried.

The invention is further illustrated, without limitation, by the following example.

Preparation of 2-Bromo-4-chloro-N-methyl-N-phenylbutanamide (a compound of Formula 2)

4-Chlorobutanoyl chloride (62 g, 440 mmol) and phosphorus tribromide (3 g) were added to a distillation flask, and heated to 90° C. Bromine (25 mL, 77.5 g, 485 mmol) was added slowly over eight hours, with the solution being allowed to decolorize between additions. The acid gases evolved were scrubbed with aqueous alkali. After the addition was complete, and the solution decolorized, a vacuum was slowly applied, and the acid gases and phosphorus tribromide scrubbed. Unreacted starting material was distilled at approximately 98° C. to 100° C./22 mmHg; and the temperature slowly increased to 105° C., where a mixture of 2-bromo-4-chlorobutanoyl chloride and 2-bromo-4-chlorobutanoyl bromide began to distill. Pure 2-bromo-4-chlorobutanoyl bromide distilled at approximately 108° C. The combined yield of 2-bromo-4-chlorobutanoyl chloride and 2-bromo-4-chlorobutanoyl bromide was 100.5 g, with a bromide/chloride ratio of approximately 6:1. The mixture of 2-bromo-4-chlorobutanoyl bromide and chloride is directly usable in the preparation of the butanamide, if desired, or may be separated and either component used.

2-Bromo-4-chlorobutanoyl bromide (80.3 g, 300 mmol) was slowly added to a solution of N-methylaniline (34.5 g, 320 mmol) and triethylamine (33.5 g, 330 mmol) in toluene (340 mL). The reaction was exothermic, and the mixture was cooled to maintain the temperature at about 40° C. After the addition was complete, the resulting thick mixture was stirred for 30 minutes, 150 mL water was added, and the mixture was stirred further. The aqueous and organic phases were separated, and the organic phase was washed with 5% hydrochloric acid and with water. The toluene was evaporated completely under slight vacuum to yield 86.3 g 2-bromo-4-chloro-N-methyl-N-phenylbutanamide (98% yield, approximately 95–96% pure). The triethylamine may be recovered from the aqueous phase by addition of base and separation.

Preparation of 4-Chloro-N-methyl-N-phenyl-2-(2-pyrrolyl)butanamide (a compound of formula 3) in Butyl Diglyme A solution of methylmagnesium chloride in butyl diglyme (4.0 L×2.8 M, 11.2 mol, 2.8 equivalents with respect to 2-bromo-4-chloro-N-methyl-N-phenylbutanamide) was added to a 12 L 4-necked round bottom flask fitted with a mechanical stirrer and two 1 L addition funnels, under a nitrogen atmosphere. 2-Bromo-4-chloro-N-methyl-N-phenyl-butanamide (1.158 kg, 3.98 mol) was added to the first addition flask, and pyrrole (0.840 L, 0.812 kg, 12.1 mol, 3.04 equivalents with respect to 2-bromo-4-chloro-N-methyl-N-phenyl-butanamide) was added to the second. The pyrrole was slowly added to the methyl-magnesium chloride/butyl diglyme solution at 45° C. to 50° C. over 3 hours, and the reaction mixture was maintained at that temperature. The resulting viscous mixture was cooled to 25° C. and stirred for 30 minutes. 2-Bromo-4-chloro-N-methyl-N-phenylbutanamide was added to the resulting mixture over a period of 2 hours while the temperature was maintained at 25° C. to 30° C., and the resulting solution was stirred for another 3 hours.

The dark-colored reaction mixture was transferred into 2.88 L (5.76 mol) 2N hydrochloric acid with rapid stirring for 1 hour. The aqueous phase was removed, and 0.8 L 15 weight % ammonium chloride in water was added to the organic phase. The resulting mixture was stirred at 35° C. to 40° C. for 10 minutes, the aqueous phase then removed, and hexanes (2.4 L) added. The resulting suspension was cooled to −20° C. and maintained at that temperature for a few minutes. The precipitate was filtered in a 300 mL sintered glass funnel and washed with hexanes (1 L). Drying of the solid under vacuum at 25° C. to 30° C. yielded 4-chloro-N-methyl-N-phenyl-2-(2-pyrrolyl)butanamide (90.84 g, 81% yield).

Preparation of 4-Chloro-N-methyl-N-phenyl-2-(2-pyrrolyl)butanamide (a compound of formula 3) in Tetrahydrofuran/Toluene/Diglyme Pyrrole (40 mL, 36.7 g, 557 mmol, 2.3 equivalents with respect to 2-bromo-4-chloro-N-methyl-N-phenylbutanamide) was added dropwise to a solution of methylmagnesium chloride in tetrahydrofuran (180 mL×2.9 M, 522 mmol, 2.1 equivalents) under a nitrogen atmosphere at a temperature of 35° C. over a period of 30 minutes. Additional tetrahydrofuran (115 mL) was added to the mixture. After the addition was complete, the suspension was stirred at 25° C. for 30 minutes and then cooled to 15° C. to 20° C. A mixture of 2-bromo-4-chloro-N-methyl-N-phenylbutanamide (76.57 g, 249 mmol), toluene (90 mL), and diglyme (50 mL) was added to the suspension in about 1 minute. The temperature increased from 30° C. to 35° C. in the first 30 minutes after addition. The resulting clear solution was stirred for 3 hours to 5 hours at room temperature and then cooled to about 5° C.

Cooled hydrochloric acid (150 mL×2 N, 300 mmol), was added over 1 minute to the reaction solution. The temperature of the suspension quickly increased to 30° C. to 35° C., and it was stirred for about 5 minutes. The resultant layers were separated and the organic layer was passed through a column of sodium hydroxide pellets. The eluent layer was again separated. The combined organic layer was stirred overnight with sodium carbonate (2.64 g) at a temperature of −5° C., then distilled to recover the cosolvent and solvents. The residual dark suspension containing the 4-chloro-N-methyl-N-phenyl-2-(2-pyrrolyl)-butanamide product was cooled to 25° C. and toluene (150 mL) was added. The resulting solution was filtered through an alumina column for decolorization and was used directly in the next step for the preparation of N-methyl-N-phenyl-2,3-dihydro-1H-pyrrolizine-1-carboxamide.

Preparation of N-Methyl-N-phenyl-2,3-dihydro-1H-pyrrolizine-1-carboxamide (a compound of formula 4)

A crude solution of 4-chloro-N-methyl-N-phenyl-2-(2-pyrrolyl)butanamide in toluene from the preceding step was added dropwise at 85° C. over 40 minutes to 1 hour to a stirred suspension of ALIQUAT® 336 (2.01 g, 2 mol % with respect to pyrrolylbutanamide) and granular sodium hydroxide (29.9 g, 750 mmol, 3 equivalents) in toluene (50 mL).

After the addition was complete, the suspension was stirred under a nitrogen atmosphere at a temperature of 85° C. for 30 minutes, then cooled to 35° C. Cooled water (200 mL) was rapidly added to the mixture and stirred for 15 minutes at 25° C. The solution was rinsed with water and the layers were separated. The organic layer was washed with water (2×100 mL), then distilled under atmospheric pressure to recover the toluene and water. The resultant solution was cooled to 50° C. and allowed to crystallize after the addition of hexane (2×50 mL) and a seed crystal. The suspension was cooled to 5° C. and stirred for 15 minutes. The resultant precipitate was filtered, washed with 100 mL of hexane, and dried under vacuum at 25° C. to yield approximately 38 g (63%) N-methyl-N-phenyl-2,3-dihydro-1H-pyrrolizine-1-carboxamide as a beige solid. This solid was recrystallized from toluene (2–2.5 mL/g) to yield large colorless crystals of N-methyl-N-phenyl-2,3-dihydro-1H-pyrrolizine-1-carboxamide, mp 112° C. to 112.5° C.

Preparation of Benzoylpiperidine (a compound of formula 5)

Benzoyl chloride (500 mL, 606 g, 4.3 mol) was added dropwise to a rapidly stirring mixture of piperidine (426 mL, 367 g, 4.3 mol), sodium hydroxide (190 g, 4.7 mol, 1.1 equivalents), toluene (1 L), and water (1.7 L) over a period of 70 minutes. After the addition was complete, the mixture was stirred at 25° C. for one hour. The organic and aqueous phases were separated, and the organic phase was washed with 2N hydrochloric acid (2×100 mL), concentrated by rotary evaporation, and distilled under vacuum to yield benzoylpiperidine as a colorless liquid which crystallized on standing. (779 g, 95% yield, bp 169° C. to 171° C.).

Preparation of 5-Benzoyl-N-methyl-N-phenyl-2,3-dihydro-1H-pyrrolizine-1-carboxamide (a compound of Formula 6) using Benzoylpiperidine N-Methyl-N-phenyl-2,3-dihydro-1H-pyrrolizine-1-carboxamide (115.35 g, 480 mmol) and toluene (100 mL) were added to a mixture of benzoylpiperidine (95.4 g, 1.05 equivalents) and phosphorus oxychloride (88 mL, 147 g, 0.96 equivalents), which had been stirred at 25° C. for 1 hour. An additional 100 mL toluene was added. The suspension was heated to a temperature of 40° C. to 45° C. for 4 hours. The resulting syrup was transferred into a rapidly stirring solution of sodium hydroxide (180 g, 4.5 mol), piperidine (1.0 mL), and water (650 mL). The temperature was maintained at 25° C. to 35° C. and the mixture was stirred for 1 hour. A mixture of toluene (100 mL), water (50 mL), and sodium hydroxide (12 g, 300 mmol) was added to the reaction flask, and the entire reaction mixture was stirred at 25° C. for 1 hour. The suspension was then heated to 75° C. and the layers were separated. The organic layer was cooled to 60° C. and hexane (100 mL) was slowly added, and the solution slowly stirred and cooled to −15° C. The precipitate was filtered, washed with toluene/hexane (150 mL, 2:1 v/v) and then with hexane (150 mL), and dried under vacuum at 25° C. to yield 5-benzoyl-N-methyl-N-phenyl-2,3-dihydro-1H-pyrrolizine-1-carboxamide (138.01 g, 83.5% yield).

Preparation of 5-Benzoyl-N-methyl-N-phenyl-2,3-dihydro-1H-pyrrolizine-1-carboxamide (a compound of formula 6) using Benzoyl Chloride N-Methyl-N-phenyl-2,3-dihydro-1H-pyrrolizine-1-carboxamide (52 g, 216 mmol), lithium carbonate (24 g, 325 mmol, 1.5 equivalents), and toluene (155 mL) were heated to a reflux temperature of 100° C. to 105° C. Benzoyl chloride (37.5 g, 267 mmol, 1.25 equivalents) was added, and the entire reaction mixture was allowed to reflux for an additional 6 hours to 8 hours. Once the reaction was complete, the mixture was cooled to 70° C. to 80° C., lithium carbonate was filtered off and the filter cake washed with 100 mL warm toluene, and the combined filtrate and washings were seeded with a few crystals of 5-benzoyl-N-methyl-N-phenyl-2,3-dihydro-1H-pyrrolizine-1-carboxamide. Hexane (100 mL) was added to the warm toluene solution to effect crystallization, and the mixture was stirred for 30 minutes; then another 80 mL of hexane was added. The mixture was stirred for 1 hour to 2 hours at room temperature, cooled to 0° C. to 5° C., filtered, washed with hexane (150 mL) and dried under vacuum at 60° C. to 70° C. to yield 5-benzoyl-N-methyl-N-phenyl-2,3-dihydro-1H-pyrrolizine-1-carboxamide (61.7 g, 82.8% yield).

Preparation of ketorolac and ketorolac tromethamine

A mixture of 34.4 g (100 mmol) 5-benzoyl-N-methyl-N-phenyl-2,3-dihydro-1H-pyrrolizine-1-carboxamide, 25 g sodium hydroxide in 25 mL water, and 80 mL methanol was refluxed for 5 hours. The mixture was cooled to room temperature, stirred under nitrogen for sixteen hours, and then diluted with 80 mL of water. The mixture was extracted with toluene (2×50 mL), and the aqueous and organic phases were separated. The aqueous phase was acidified with 6 N hydrochloric acid (110 mL). The resulting precipitate was extracted several times with dichloromethane (1×150 mL), (1×75 mL), (1×50 mL). The combined extract was treated with FILTROL® (activated clay decolorizing agent) (4.5 g) for 30 minutes, filtered, and concentrated by atmospheric distillation. Hexane (190 mL) was added and the entire mixture allowed to cool to room temperature and then further cooled to 0° C. to −5° C. The product, 5-benzoyl-2,3-dihydro-1H-pyrrolizine-1-carboxylic acid (ketorolac) was collected by filtration, washed with 100 mL of hexane/dichloromethane (7:3 v/v), and dried at 60° C. to 70° C. under vacuum, to yield ketorolac (21.3 g, 83.4% yield), mp 152° C. to 162° C.

Ketorolac (25 g) and 11.9 g tromethamine were dissolved in 175 mL methanol. The solution was filtered and the filter washed with 40 mL methanol. The resulting solution was concentrated by vacuum distillation. Ethyl acetate (1×172 mL), (1×200 mL) was added to the solution to precipitate the ketorolac tromethamine; and the solution was cooled to room temperature for two hours, cooled further to 0° C., and filtered. The precipitate was washed with ethyl acetate/methanol (4:1 v/v) and dried under vacuum at a temperature of approximately 65° C., to yield ketorolac tromethamine (35.0 g, 95% yield).

While this invention has been described in conjunction with specific embodiments and examples, it will be evident to one of ordinary skill in the art, having regard to this disclosure, that equivalents of the specifically disclosed materials and techniques will also be applicable to this invention; and such equivalents are intended to be included within the following claims.

What is claimed is:

1. A process for preparing ketorolac of formula (I), (I)

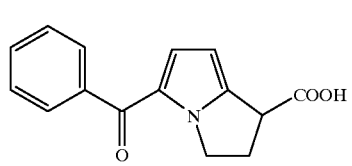

comprising hydrolyzing a compound of the formula

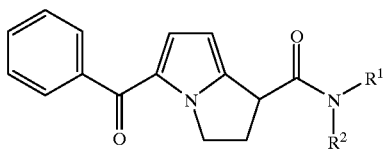

where $R^1$ is alkyl and $R^2$ is optionally substituted phenyl, with a strong base.

2. The process of claim 1 where $R^1$ is methyl.

3. The process of claim 1 where $R^2$ is phenyl.

4. The process of claim 1 where the strong base is an alkali metal hydroxide.

5. The process of claim 1 where the step of hydrolyzing is carried out in an alkanol.

6. The process of claim 5 where the alkanol is methanol.

7. The process of claim 1 further comprising the formation of a pharmaceutically acceptable salt of ketorolac by reaction of the ketorolac with a pharmaceutically acceptable base.

8. The process of claim 7 where the pharmaceutically acceptable base is tromethamine.

* * * * *